United States Patent [19]

Takahashi et al.

[11] Patent Number: 4,792,549

[45] Date of Patent: Dec. 20, 1988

[54] COMPOSITION OF AMINO ACIDS

[75] Inventors: Akira Takahashi, Matsudo; Yoshiyuki Shimamura, Ichikawa; Hide Kobayashi, Matsudo; Shigeo Okonogi, Tokyo; Takuji Kawashima, Kawasaki; Minoru Igarashi, Misato, all of Japan

[73] Assignee: Morinaga Milk Industry Co., Ltd., Tokyo, Japan

[21] Appl. No.: 946,031

[22] Filed: Dec. 24, 1986

[30] Foreign Application Priority Data

Jan. 13, 1986 [JP] Japan .................................. 61-4834

[51] Int. Cl.$^4$ ................. A61U 31/195; A61U 31/415
[52] U.S. Cl. ..................................... 514/400; 514/561
[58] Field of Search .............................. 514/400, 561

[56] References Cited

U.S. PATENT DOCUMENTS 3,950,529 4/1976 Fischer et al. ..................... 514/400

Primary Examiner—Stanley J. Friedman
Attorney, Agent, or Firm—Oblon, Fisher, Spivak, McClelland & Maier

[57] ABSTRACT

A composition of amino acids which can be orally administered to patients of hepatic and renal diseases for increasing serum albumin, haemoglobin and branched amino acids in serum and for improving nitrogen metabolism and which comprises 32.0 weight parts of amino acid selected from the group consisting of cystine, cysteine, methionine and a mixture thereof, 14.0–20.7 weight parts of alanine, 18.7–28.0 weight parts of aspartic acid and 15.5–23.4 weight parts of glycine in 100 weight parts of total amino acids contents in the final product.

2 Claims, 1 Drawing Sheet

COMPOSITION OF AMINO ACIDS

TECHNICAL FIELD

The present invention relates to a new composition of amino acids, more particularly, relates to a composition of amino acids to be orally administered to the patients of hepatic or renal diseases to improvide nitrogen metabolism.

BACKGROUND

Abnomal nitrogen metabolism is often observed in hepatic diseases such as liver cirrhosis and renal diseases such as chronic renal failure. There has not been effective medicines for such symptom. In a mild case, dietetic therapy has been applied and when the symptom progresses, fluid therapy has been applied by administrating infusion fluid containing amino acids mixture.

Various infusion fluids containing amino acids have been known. For example, an amino acids infusion fluid for cancer patients is disclosed in Japanese Unexamined Patent Application Gazette No. 55 (1980)-35049. The infusion fluid disclosed in this reference contains all of 8 kinds of essential amino acids for closely imitating the composition of plasma amino acids of a healthy human.

To liver cirrhosis patients it is recommended in Japanese Unexamined Patent Application Gazette No. 56(1981)-27493 to administrate an infusion fluid containing amino acids which are generally deficient in liver cirrhosis in order to recover normal amino acids composition in blood of a healthy human. In Japanese Unexamined Patent Application Gazettes Nos. 55(1980)-36457 and 54(1979)-26324, infusion fluids for liver cirrhosis patients containing relatively larger parts of branched chain amino acids such as leucine, isoleucine and valine and relatively smaller parts of tyrosine and phenylalanine.

The conventional amino acids infusion fluids can be expected to have temporary effects, however, it has been a question whether the conventional infusion fluids may actually improve nitrogen metabolism for a long period of time.

The inventors of the present invention have extended their efforts for seeking a simple composition of amino acids which can be orally administered to patients of hepatic and renal diseases on the view points that:

(1) Aspartic acid and alanine will be necessary to supplement metabolic pool of amino acids and to promote internal formation of albumine by glutamic oxaloacetic transaminase (GOT) and glutamic pyruvic transaminase (GPT).
(2) Glycine will be necessary to be bonded with aromatic amino acids so as to produce hippuric acid which can be excreted in urin, since benzene rings of aromatic amino acids can be hardly decomposed.
(3) Glycine will be also necessary for the reason that synthesis of haemoglobin can be promoted by incorporateing free irons in body fluids in porphirin rings formed by bonding of carbonic acids of glycine and carbonyl group of succinic acids.
(4) Crystine will be necessary as a donor of methyl radical for the purposes described in the above items (1) and (3).

As the results, the inventors of the present invention found a new composition of amino acids which is effective for increasing serum albumin, haemoglobin and branched chain amino acids and for improving nitrogen metabolism for a long period of time. The present invention is based on this discovery.

SUMMARY OF THE INVENTION

It is an object of this invention to provide a composition of amino acids which is effective for increasing serum albumin, haemoglobin and branched chain amino acids and for improving nitrogen metabolism in patients of hepatic and renal diseases and which can be orally administrated.

It is another object of this invention to provide a simple composition of amino acids which can be prepared in simple processes.

In accordance with this invention the composition of amino acids contains 32.0–48.0 wieght parts of amino acid selected from the group consisting of cystine, cysteine, methionine and a mixture thereof, 14.0–20.7 weight parts of alanine, 18.7–28.0 weight parts of aspartic acid and 15.5–23.4 weight parts of glycine in 100 weight parts of total amino acids contents in the final product.

DETAILED DESCRIPTION OF THE INVENTION

Figure 1:
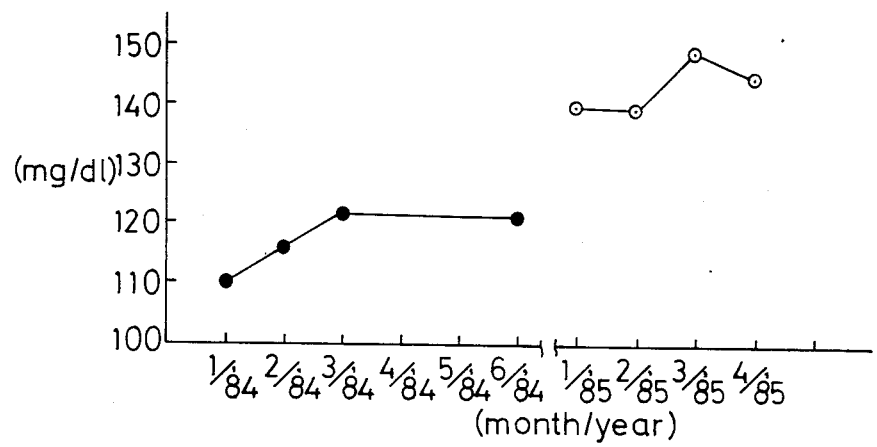
FIG. 1 shows time course of varies of cholesterol level.

In this invention not only amino acids but also thier salts, such as sodium asparaginate, and thier delivertives can be utilized. Amino acids other than alanine, aspartic acid and glycine can be selected from the group consisting of cystine, cysteine, methionine and a mixture thereof. The contents of such amino acids in the composition can be generally determined from the necessary quantities of essencial amino acids in view of that serum albumin in the patients is 60–90% of that of a healthy human. However, it is preferable that the contents of the amino acids in the composition are determined taking variable factors such as weights, conditions, labor of the respective patients in consideration. In order to avoid the troublesome job to compound respective amino acids for each individual patient, a composition of amino acids having a fixed ratio of the respective components is prepared and a dose of the composition can be varied so that any component of the composition is insufficient for a specific patient. In view of the foregoing points, it has been found that the most preferable composition of amino acids is 0.5 weight parts of glycine, 0.4 weight parts of alanine and 0.6 weight parts of aspartic acid to 1 weight part of cysteine.

The composition of amino acids in accordance with this invention can be prepared by homogeneously mixing a given quantities of amino acids components in solid state. Mixing can be carried out, for example, by a V-shaped mixer.

If occasion demands, lipids, vitamins and minelals can be added to the composition of this invention. When minor quantities of additives such as vitamins are to be added, such additives are once dissolved into aqueous solution of amino acids, then the resulted solution is subjected to freeze drying to obtain a homogeneous mixture thereof.

In general 1–10 g/day, preferablly 1.5–4.0 g/day, of the composition of amino acids of the present invention can be administered to an adult patient, however, it is preferable that quantity of administration is determined in accordance with the conditions of diseases, nutritious conditions, ages and weights of the respective patients.

For better understanding of this invention, some exemplefying tests will be described hereunder.

[SUBJECTS]

Patients of liver cirrhosis were divided into two groups as follows:

Group I: 5 patients of light symptoms consisting of 3 men and 2 wemen
(average age: 57.5)

| VALUES MEASURED | |
|---|---|
| serum albumin | 3.0 g/dl or more |
| serum cholesterol | 120 mg/dl or more |
| prothronbin activity (PT activity) | 70% or more |
| indocyanine green retention (ICG) | 30% or less |
| number of thrombocytes | 100,000 or more |

Group II : 6 patients of medium symptomes consisting of 4 men and 2 wemen (average age: 54.5)

| VALUES MEASURED | |
|---|---|
| serum albumin | less than 3.0 g/dl |
| serum cholesterol | less than 120 mg/dl |
| prothronbin activity (PT activity) | less than 70% |
| indocyanine green retention (ICG) | more than 30% |
| number of thrombocytes | less than 100,000 |

[TEST 1]

To the patients of Group I, 1.5 g/day of the composition of amino acids prepared in Example 2, ordinary meal and 500 g/day of cow's milk were given for 12 weeks. Total protein, albumin and cholesterol levels in serum and value of zinc sulfate turbidity test (ZTT) were measured by means of routine methods at the begining and every 4 weeks thereafter of the test period. The results are shown in Table 1.

In comparison of total protein and albumin levels in serum, it can be seen that the values after administration of the composition of amino acids of this invention are equal or larger than those at the begining of this test in all patients, and it has been found that the composition of amino acids of Example 2 is effective for increasing the total protein and albumin levels in serum. As the results of statistical analysis of the mean values before administration of the composition and mean values at each time of measurement after administration of the composition, significant differences are observed on the level of significance of 1%.

Tendency of increasing cholesterol level in serum is also observed by administration of the composition, and statistical analysis of the mean values before administration of the composition and means values at each time of measurement show significant differences on the level of significance of 5%.

TABLE 1

| | | Patient No. | | | | | mean |
|---|---|---|---|---|---|---|---|
| | | 1 | 2 | 3 | 4 | 5 | value |
| serum protein (g/dl) | before | 7.8 | 7.8 | 7.0 | 7.9 | 6.7 | 7.4 |
| | 4 weeks | 7.7 | 8.2 | 7.3 | 8.4 | 7.2 | 7.3 |
| | 8 weeks | 8.0 | 8.6 | 7.7 | 8.3 | 7.2 | 8.0 |
| | 12 weeks | 8.0 | 8.0 | 8.0 | 7.9 | 7.2 | 7.8 |
| serum albumin (g/dl) | before | 3.7 | 4.3 | 4.0 | 4.6 | 3.4 | 4.0 |
| | 4 weeks | 4.0 | 4.5 | 4.2 | 4.8 | 3.8 | 4.3 |
| | 8 weeks | 4.0 | 4.7 | 4.2 | 4.8 | 3.8 | 4.3 |
| | 12 weeks | 4.1 | 4.5 | 4.2 | 4.6 | 3.6 | 4.3 |

TABLE 1-continued

| | | Patient No. | | | | | mean |
|---|---|---|---|---|---|---|---|
| | | 1 | 2 | 3 | 4 | 5 | value |
| serum cholesterol (mg/dl) | before | 177 | 133 | 151 | 176 | 155 | 158 |
| | 4 weeks | 189 | 155 | 143 | 177 | 184 | 170 |
| | 8 weeks | 201 | 163 | 153 | 163 | 170 | 171 |
| | 12 weeks | 211 | 175 | 153 | 186 | 166 | 178 |
| ZTT value (unit) | before | 30.8 | 17.8 | 9.8 | 14.0 | 17.9 | 18.1 |
| | 4 weeks | 23.6 | 13.8 | 7.7 | 9.0 | 13.1 | 13.4 |
| | 8 weeks | 24.5 | 16.3 | 9.4 | 13.3 | 11.3 | 15.0 |
| | 12 weeks | 26.5 | 14.4 | 8.4 | 10.2 | 11.9 | 14.3 |

ZTT values are decreased by administration of the composition, and statistical analysis of the mean values before administration of the composition and mean values at each time of measurement after administration of the composition show significant differences on the level of significance of 5%.

Accordingly the composition of amino acids of this invention is found to be effective to increase total protein, albumin and cholesterol levels in serum and to decrease ZTT value in light symptom patients of hepatic disease.

[TEST 2]

To the patients of Group II, 3.0 g/day of the composition of amino acids prepared in Example 2, ordinary meal and 500 g/day of cow's milk were given for 8 weeks. The ZTT values and haemoglobin levels were measured by means of the routine methods at the begining and every 4 weeks. The results are shown in Table 2.

TABLE 2

| | | Patient No. | | | | | | mean |
|---|---|---|---|---|---|---|---|---|
| | | 1 | 2 | 3 | 4 | 5 | 6 | value |
| ZTT value (unit) | before | 23.7 | 15.2 | 18.2 | 17.6 | 22.6 | 24.1 | 20.2 |
| | 4 weeks | 21.4 | 11.4 | 17.6 | 14.9 | 20.2 | 21.7 | 17.9 |
| | 8 weeks | 21.8 | 12.0 | 15.5 | 13.3 | 17.6 | 23.1 | 17.2 |
| haemo-globin (g/dl) | before | 13.5 | 14.8 | 15.3 | 11.0 | 14.1 | 12.7 | 13.6 |
| | 4 weeks | 13.5 | 16.7 | 16.1 | 12.8 | 14.7 | 14.6 | 14.7 |
| | 8 weeks | 14.3 | 17.5 | 16.1 | 12.6 | 14.8 | 14.4 | 15.0 |

It will be noted that ZTT values are apparently decreased on all of the subjects after administration of the composition of this invention. Statistical analysis of the mean values before administration of the composition and the mean values at each time of measurement after administration of the composition show significant differences on the level of significance of 5%.

Also it will be noted that haemoglobin levels are apparently increased in all of the subjects after administration of the composition of this invention. Significant differences are observed on the level of significance of 1% in statistical analysis of the mean values before administration of the composition of this invention and the mean values at each time of measurement after administration of the composition.

Consequently the composition of amino acids of this invention is found to be effective to decrease ZTT value and to increase haemoglobin level in the patients of liver cirrhosis of medium symptoms.

[Test 3]

To the patients of Group I after Test 1, 2.25 g/day of the composition of amino acids prepared in Example 2, ordinary meal and 250 g/day of cow's milk were given for 8 weeks. The values of serum albumin were measured by means of the routine methods at the begining and every 4 weeks in the test period. The results are shown in Table 3.

TABLE 3

|  |  | Patient No. |  |  |  |  | mean value |
|---|---|---|---|---|---|---|---|
|  |  | 1 | 2 | 3 | 4 | 5 |  |
| serum albumin (g/dl) | before* | 4.1 | 4.5 | 4.2 | 4.6 | 3.6 | 4.2 |
|  | 4 weeks | 3.7 | 4.4 | 4.6 | 4.9 | 3.7 | 4.3 |
|  | 8 weeks | 3.7 | 4.2 | 4.6 | 4.5 | 3.8 | 4.2 |

*The values in this line are those after 12 weeks shown in Table 1.

From the results in this test it will be apparent that almost no significant difference in serum albumin levels is observed when an additional amino acid is added to the composition of amino acids of this invention. Therefore it is exemplified that a composition containing at least cystine, crysteine, methionine, alanine and aspartic acid is effective. [Test 4]

During the term from January to April in 1985, a patient of liver cirrhosis was administrated 1.5 g/day of the composition of amino acids prepared in same manner as described in Example 2 in addition to ordinary meal. The patient had been administrated conventional amino acid preparation THF (cf. Nihon Rinsho, Vol. 40, No. 4, page 83, 1982) for liver failure having a composition (per 100 parts of amino acids composition as shown in Table 4) in quantity of 18 g/day (from September 16 to November 3, 1983) and 9 g/day (from November 4, 1983 to Aug. 10, 1984), in addition to ordinary meal.

TABLE 4

| isoleucine | 12.93 | alanine | 11.81 |
|---|---|---|---|
| leucine | 13.28 | arginine | 12.93 |
| valine | 12.51 | histidine | 4.36 |
| tryptophan | 0.99 | proline | 7.45 |
| phenylalanine | 0.42 | serine | 3.65 |
| tyrosine | 0.84 | glycine | 7.59 |
| lysine | 5.55 | asparagine | 0.28 |
| methionine | 0.91 | cysteine | 0.28 |
| threonine | 4.22 |  |  |

During the term of this test, serum cholesterol level and ZTT value were measured in accordance with the routine methods on every last day of the months. The results are shown in FIGS. 1 and 2 together with the values measured at every last day of January, February, March and June of 1984 during the preceding treatment.

Figure 2:
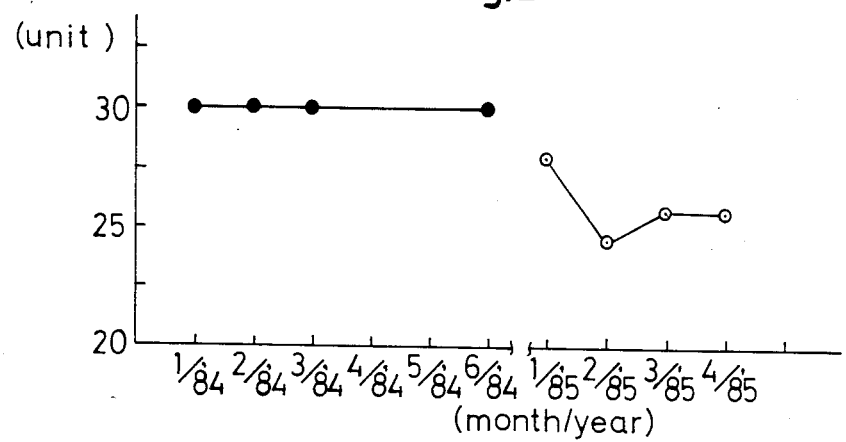
FIG. 2 shows time course of varies of ZTT value.

In FIG. 1, varies of serum cholesterol level is shown wherein the ordinate shows quantity of serum cholesterol in g/dl and the abscissa shows the day on which the values were measured. In FIG. 2, varies of ZTT values is shown wherein the ordinate shows ZTT value in unit and the abscissa shows the day on which the values were measured. In both of the drawings, ●—● shows the values in the term wherein THF was given and ⊙—⊙ shows the values in the term wherein the composition of amino acids of this invention was given.

As will be apparent from FIG. 1, serum cholesterol level were nearly 120 mg/dl and no increasing tendency cannot be observed during the term wherein THF was given, however, after administration of the composition of amino acids of this invention the values were inreased and maintained over the level of 140 mg/dl.

On the other hand, it will be apparent that ZTT values were stable at 30 units during the term wherein THF was given, whereas the values were decreased to about 26 units after the composition of amino acids of this invention was administrated.

From the foregoing results, it has been found that the composition of amino acids of this invention has remarkable effect for increasing serum cholesterol level and decreasing of ZTT value in patient of liver cirrhosis.

Now some examples will be described hereunder for better understanding of the present invention.

[EXAMPLE 1]

Using a V-shaped mixer, 400 g of commercially available L-cystine, 160 g of alanine, 240 g of L-aspartic acid and 200 g of L-glycine respectively in pure crystalline state were homogeneously mixed to obtain approximately 1 Kg of composition of amino acids.

[EXAMPLE 2]

To 5 l of water, 240 g of commercially available pure L-aspartic acid was disolved, and a minor amount of vitamin B12 was added to the solution, and after homogenizing the resulted solution it was subjected to freeze drying. To whole amount of the resulted powder, 160 g of commercially available L-alanine, 400 g of L-cystine and 200 g of L-glycine respectively in pure crystellien state were added, and homogeneously mixed with a V-shaped mixer to obtain approximately 1 Kg of the amino acids composition containing vitamin B12 of this invention.

[EXAMPLE 3]

Approximately 1 Kg of the amino acids composition containing vitamin B12 and L-leucine was prepared in the same manner as in example 2 except that 500 g of commercially available L-leucine was further added.

[EXAMPLE 4]

Using a V-shaped mixer, 200 g of commercially available L-cystine, 200 g of L-cysteine, 160 g of L-alanine, 240 g of L-aspartic acid and 200 g of L-glycine respectively in pure crystalline state were mixed to obtain approximately 1 Kg of the amino acids composition.

[EXAMPLE 5]

Using a V-shaped mixer, 200 g of commercially available L-cystine, 100 g of L-cysteine, 100 g of L-methionine, 160 g of L-alanine, 240 g of L-aspartic acid and 200 g of L-glycine were homogeneously mixed to obtain approximately 1 Kg of amino acids composition.

[EXAMPLE 6]

Using a V-shaped mixer, 400 g of commercially available L-cystein, 160 g of L-alanine, 240 g of L-aspartic acid and 200 g of L-glycine respectively pure crystalline state were homogeneously mixed to obtain approximately 1 Kg of amino acids composition.

The effects of the composition of amino acids of this invention are as follows:

(1) In spite of that the composition of this invention is simple, nitrogen metabolism caused by hepatic or renal diseases involving abnomal nitrogen metabolism can be improved.

(2) As the result of improvement of nitrogen metabolism, decrease of blood anmonia, promotion of synthesis of serum albumin, increase of serum cholesterol, decrease of ZTT value, promotion of reuse of free haemoglobin can be achieved, this in turn effective for alleviation of various symptoms in hepatic or renal diseases.

(3) Cerebral symptom accompanied with abnormal nitrogen metabolism can be prevented.

We claim:

1. An amino acid-containing composition suitable for oral administration to patients having hepatic and renal diseases, which consists essentially of glycine, alanine, aspartic acid and an amino acid selected from the group consisting of cystine, cysteine, methionine and a mixture thereof in a ratio of 0.5:0.4:0.6:1 by weight part in the final product.

2. The amino acid-containing composition of claim 1, wherein said amino acid is cystine, cysteine or a mixture thereof.

* * * * *